United States Patent [19]
Schmidt

[11] Patent Number: 5,928,635
[45] Date of Patent: *Jul. 27, 1999

[54] PROCESS FOR PRODUCING ACTIVE AGENT COMPLEXES

[76] Inventor: Karlheinz Schmidt, Äussere Weiler Str. 12, 72810 Gomaringen, Germany

[ * ] Notice: This patent is subject to a terminal disclaimer.

[21] Appl. No.: 08/899,270

[22] Filed: Jul. 23, 1997

Related U.S. Application Data

[62] Continuation of application No. 08/313,113, Dec. 7, 1994, abandoned, which is a continuation-in-part of application No. 07/849,083, filed as application No. PCT/EP92/00822, Apr. 11, 1992, abandoned.

[51] Int. Cl.[6] .................................................... A61K 45/05
[52] U.S. Cl. ....................... 424/85.1; 424/520; 424/549; 514/21; 530/344; 530/351; 530/356
[58] Field of Search ..................................... 530/356, 344, 530/351; 514/21; 424/85.1, 520, 549

[56] References Cited

U.S. PATENT DOCUMENTS

| | | | |
|---|---|---|---|
| 4,294,753 | 10/1981 | Urist | 424/95 |
| 4,404,134 | 9/1983 | Becker et al. | |
| 4,472,840 | 9/1984 | Jefferies | |
| 4,627,982 | 12/1986 | Seyedin et al. | |
| 4,642,120 | 2/1987 | Nevo et al. | 623/16 |
| 4,693,718 | 9/1987 | Urry et al. | |
| 4,703,108 | 10/1987 | Silver et al. | 530/356 |
| 4,732,155 | 3/1988 | Zetter et al. | |
| 4,832,686 | 5/1989 | Anderson | |
| 4,863,732 | 9/1989 | Nathan et al. | |
| 4,925,924 | 5/1990 | Silver et al. | |
| 4,932,973 | 6/1990 | Gendler | |
| 4,950,483 | 8/1990 | Fasandel et al. | 424/422 |
| 4,973,466 | 11/1990 | Reich | |
| 5,019,087 | 5/1991 | Nichols | |
| 5,024,841 | 6/1991 | Chu et al. | 530/356 |
| 5,041,138 | 8/1991 | Vacanti et al. | |
| 5,118,791 | 6/1992 | Burnier | 530/13 |
| 5,556,430 | 9/1996 | Gendler | |

FOREIGN PATENT DOCUMENTS

| | | |
|---|---|---|
| 271668A1 | 6/1988 | European Pat. Off. |
| 2637502A1 | 4/1990 | European Pat. Off. |
| 3936568 | 8/1991 | European Pat. Off. |
| 2137209 | 10/1984 | United Kingdom |
| 2137209 | 10/1989 | United Kingdom ..................... 623/16 |
| 84/00540 | 2/1984 | WIPO |
| 88/07078 | 9/1988 | WIPO |
| 90/00060 | 1/1990 | WIPO |
| 9106324 | 5/1991 | WIPO |

OTHER PUBLICATIONS

Furcht et al., Lab Investigation, vol. 55(5), pp. 505–509(1916) Editorial Critical Factors . . .
International Search Report dated Dec. 9, 1992.
Dijke et al., "Growth Factors For Wound Healing" (1989) Biotechnology, V. 7,pp. 793–798.
Alberts et al., "Molecular Biology of Cell" (1984) Garland Publishing, Glossary Defining "Lytokine".

*Primary Examiner*—Cecilia J. Tsang
*Assistant Examiner*—Patrick R. Delaney
*Attorney, Agent, or Firm*—Blank Rome Comisky & McCauley LLP

[57] ABSTRACT

The invention relates to a process for producing active agent complexes from at least one initial complex having components in which the initial complex is caused at least partially to assume a homogeneous phase by means of a denaturing process and by being broken into its components, said phase having at least partially the components with an at least partially altered structure. By means of a renaturing process, a final complex is formed from at least one predetermined component together with at least one part of the homogeneous phase. Said final complex forms the active agent complex after at least one cycle consisting of a denaturing and renaturing process. The process of the invention provides active agent complexes, the effect of which can be triggered at the desired place and for a desired time even when short-lived active agents are used in a living organism.

28 Claims, No Drawings

PROCESS FOR PRODUCING ACTIVE AGENT COMPLEXES

This is a continuation of application Ser. No. 08/313,113, filed on Dec. 7, 1994, now abandoned, which is a continuation-in-part of application Ser. No. 07/849,083 filed on Sep. 17, 1992, now abandoned, and is a §371 of PCT/EP92/00822 filed on Apr. 11, 1992.

BACKGROUND OF THE INVENTION

The invention relates to a process for producing active agent complexes having the features of being produced by the process of forming a homogenous phase of a selected tissue by means of a denaturing process, concentrating selective components of the homogeneous phase, adding the concentrated selected components back to the homogeneous phase then renaturing the components to form an active agent complex. The invention also relates to an active agent complex produced according to the process for producing biological parts, and to its use.

Active agent complexes are complexes of the type having at least two components, at least one of the components being an active agent. Active agents develop their effects generally as a result of the fact that they interact with cells as the carriers of living functions. Thus, the active agents can be produced endogenously, i.e., inside the body as products of cellular metabolism or they can be supplied to the body from the exterior as food, environmental substances or medicines. In all cases, the interaction with one or more target structures in the organism is necessary in order to achieve the biological effect.

In the case of active agents produced endogenously, the spatial and chronological distances between their production and their effect may differ greatly. Thus, for example, hormones can act over great distances or even, as tissue hormones, develop their activities over very short distances. In order to render variations in the signal flow between the production site and action site of an active agent possible in the short term, in the case of many endogenously produced active agents, such as hormones, neurotransmitters, cytokinins, etc. for example, the half-life value is short, the result of which is that the useful life of the active agents in the propagation medium is very short. The half-life values in blood, for example, are in the region of minutes to seconds for many active agents.

This production and effect characteristic with very rapid decomposition kinetics is usually advantageous for the endogenous active agents since the production can rapidly be adapted to the requirement but it is a serious problem for the exogenous application of these short-lived active agents, since, in many cases, the exogenous application of important active agents is impossible because their half-life values are so short that interaction with the corresponding target structures no longer occurs and thus the effect does not take place.

SUMMARY OF THE INVENTION

In the case of a known process for producing active agent complexes, an initial complex having as components inter alia one or more required active agents is subjected to a denaturing process, the initial complex being caused at least partially to assume a homogeneous phase by being broken into its components and in the case of which individual components and in the case of which individual components change their structure at least partially. In the case of this denaturing process, moreover, the respective initial complex is physiologically inactivated. Each required active agent is then isolated from the homogeneous phase and correspondingly "collected" in order to obtain the active agent complex. Active agent complexes produced according to this known process are not suitable for using short-lived active agents in a living organism.

The invention is therefore based on the object of providing a process for producing active agent complexes of which the effect can be triggered in a living organism at the required activity site and for a required period even when short-lived active agents are used.

In accordance with the invention this object is achieved by a process for producing an active agent complex from at least one initial complex or tissue which has in the tissue the components of the active agent complex. The components are isolated by the process of forming at least a partially homogeneous solution of the tissue by means of a mild denaturing process that breaks the tissue down into the tissue's components. The desired active ingredient is concentrated in its denatured form and added back to part of the denatured tissue solution. The concentrated active ingredient and denatured tissue solution is then renatured to form an active complex. As a result of the fact that a final complex is formed by means of a renaturing process from at least one predetermined component together with at least part of the homogeneous phase and that the final complex forms the active agent complex after at least one cycle consisting of a denaturing and renaturing process, it is possible to render active agents with short half-life values usable for exogenous application. Each predetermined component is thus an active agent which the active agent complex produced according to the invention is to comprise when it is subsequently used in the organism. What is to be understood by a renaturing process is in general the removal of the means provided for the denaturing process.

Thus the active agent complexes produced in this manner have the advantage that each active agent they contain is purposefully released only when it is in the organism. There may be a single active agent. However, a plurality of active agents can also be present in the complex. Each cycle of a denaturing-renaturing process is per se a type of enrichment (concentration) step relative to the active agent predetermined in each case. If a plurality of cycles are performed, any predetermined active agent in the active agent complex can be enriched in such a way that, when it has been introduced into an organism, it is effective for a precisely defined and predeterminable time. As a result thereof active agents which are per se endogenous, which are only produced in small amounts in the living organism and which under certain circumstances are only present in traces in an initial complex necessary for the application of the process according to the invention, are amenable to exogenous application. It is thus also within the scope of the process according to the invention to enrich a plurality of active agents present as components in the initial complex independently of one another in very different concentrations in order to form the active agent complex.

In a preferred embodiment of the process according to the invention, any predetermined component from part of the homogeneous phase is depleted, enriched or isolated. Thus any number of parts can be formed from the homogeneous phase.

Preferably, the homogeneous phase is divided into two parts, each predetermined component from the one part of the homogeneous phase being depleted, enriched or isolated and combined with the other part of the homogeneous phase.

In the case of a further preferred embodiment of the process according to the invention, at least one further component not present in the initial complex is added to the active agent complex. As a result thereof, it is possible to combine endogenously produced active agents with further active agents, which may be natural or synthetic, in such a way that completely novel, predeterminable effects can be achieved by using the active agent complex according to the invention.

The initial complex used in the application of the process according to the invention can be formed by the use of animal or human cells, tissues or organs. However, it can also be formed from microbial or vegetable cell cultures or organisms or produced synthetically.

Furthermore, with the application of the process according to the invention, the initial complex can be denatured reversibly such that irreversible alteration of the initial complex or one of its components does not occur, which facilitates the renaturing process.

Preferably, acids, salts, chaotropic substances, such as, for example, urea, detergents, etc., can be used in the denaturing process. In accordance with the invention, renaturing occurs by removing the denaturing means, it being possible to use physical, chemical or biological processes.

By using the process according to the invention it is further possible to prepare an active agent complex for producing biological parts, in particular organs for living beings. An active agent complex for this purpose is described in DE-OS 39 36 568. The active agent complex comprises at least four different components (structural component, soluble recruiting component, insoluble adhesion component, growth and maturation component) which materially are not identical to one another. If fibronectin is placed in solution in order to form the recruiting component, the adhesin component must be formed from another substance which is different from fibronectin and is insoluble. The same applies in the reverse case, if fibronectin is used in the insoluble form for the adhesion component. The components in question which differ from one another are adapted to target cells and are used for constructing the biological parts from endogenous cells.

Biological parts occupy a given amount of space for performing their functions. Frequently, their function is associated with a given geometry and the biological parts have given limits within which they fulfill their function. Similarly, this applied for the biological parts produced by means of the active agent complex according to the invention. The active agent complex used for the production process performs this function using a structural component which, on the one hand, performs a space-saving function and, on the other, enables a geometrical shape to be predetermined within which the biological part produced performs its function.

DETAILED DESCRIPTION OF THE PREFERRED EMBODIMENTS

In the case of a preferred embodiment of the structural component of the active agent complex it is predominantly a macromolecular, three-dimensional matrix which, together with water and salt, can be in the form of gel of differing swelling states. Thus, for example, proteoglycan gels can be used as a matrix. A network of fibers, such as different types of collagens or elastin for example, can also form the structural component. Likewise, combinations of gels with intercalary fibers are suitable as composite active agents. For the different applications for producing biological parts, the structural component is manufactured in different ways in order to be used such that it can be cut, ground, plastically deformed or cast, for example, as a non-woven fabric, as a gel body or fluid gel.

The structural component is adapted to the requirements of the biological part to be produced since a given specificity exists between the cellular and extracellular portions of biological parts. Sources for the production of the structural component are therefore predominantly the extracellular materials of different tissues or organs, i.e. for example for the production of skin cutaneous proteoglycans and fibre proteins are used for producing the structural component of skin, the spleen-specific proteoglycans and fibre proteins are used for producing the spleen, bone-specific proteoglycans and fibre proteins are used for producing bones, etc. The structural component can also comprise metallic, ceramic, vitreous, polymer or adipose carrier materials by means of which the geometrical, mechanical, chemical or other properties of the structural component can be modified. Thus the carrier material can be present together with the structural component in the solid, porous, membrane, micella, viscous or fluid form depending on the requirements resulting from the production of the biological part and its subsequent function.

In the case of a further preferred embodiment of the active agent complex according to the invention, the latter develops its effect for producing the biological parts substantially only temporarily, i.e. the active agent complex is formed in such a way that it can be controlled and broken down chronologically and no longer exists when the biological part has been produced. The decomposition speed of the active agent complex can thus be predetermined by different cross-linkings of the polymer matrix and/or the addition of (enzyme) inhibitors and/or immunosuppressants and/or anti-inflammatory substances. The inhibitors used in this case can be low-molecular compounds occupying/comprising the active center of the decomposing enzyme but they can also be complexing agents which per se form an essential cofactor of the enzyme, or they can be neutralizing antibodies. Further inhibition mechanisms are possible. The following can be used in this case as anti-inflammatory and/or immunosuppressant additives: phospholipase inhibitors, such as steroids, for example, cyclooxygenase inhibitors, such as indomethacin, for example, lipoxygenase inhibitors, such as nordihydroguaiaretic acid for example, immunosuppressants of the cyclosporin type and/or of the antithymocyte globulin-type, et cetera.

Living cells of the required type are to be concentrated in the vicinity of the structural component in order to produce biological parts. For this purpose, the structural component of the active agent complex contains one or more recruiting components by means of which the required/desired cells can be stimulated to perform the set/directed movement. Chemotactic substances (chemotaxins) are suitable as recruiting components.

The chemotactic substances suitable in each case have been described for a number of cells and can be isolated from human, animal, vegetable or microbial sources or even produced by chemical synthesis or biotechnological processes. If the structural component produced externally of the body of the living being is introduced with its recruiting component(s) into an organism and/or is combined with target cells externally of the organism, a concentration gradient builds up towards which the target cells are oriented, the respective recruiting component(s), with the specific detecting structures interacting with/on the target cells, which are also known as receptors. In the event of the biological part to be produced being composed of a plurality of cell types the structural component comprises a plurality of recruiting components in the form of chemotactic substances according to the number of the cell types.

The specificity of the respective recruiting component for the different target cells and the extent of the chemotactic substances activities are determined by means of investigations in the case of which the directed migration of the desired cells through defined filter pores is measured in a chamber under the effect of a gradient of the chemotactic substances. By means of investigative techniques of this type, the active agent system can be biologically standardized as regards its respective recruiting component which is important for the production of the active agent complex on an industrial scale.

Peptides such as N-F-Met-Leu-Phe and/or, for example, metabolites of arachidonic acid, such as leucotrienes, are used, for example, as chemotactic substances by means of which given cells can be attracted from the blood or phagocytes. Proteins, such as a protein attracting mesenchyme cells have a chemotactic substances effect on connective tissue cells in particular.

In addition to the specificity of the respective recruiting component for the desired/required target cell and the extent of the chemotactic substances activity, the duration for which the chemotactic substances concentration gradient builds up and is maintained is an important value. In the case of the active agent complex according to the invention, these kinetics are adapted to the requirements for producing the biological parts, by a controllable release of the respective recruiting component from the structural component. In this respect, the speed of decomposition itself plays a role as does the type of connection between the structural component and the respective recruiting component, e.g., whether it is a covalent or an associative connection. If the connection is covalent, a slower build-up and a longer maintenance of the chemotactic substances gradient is achieved than in the case of a merely associative connection by ionic forces or hydrogen bridge bonding. However, in most cases the recruiting of the cells for producing the biological part occurs more rapidly than the decomposition of the structural component since the immigrant cells contribute quite substantially to the decomposition of the proteoglycan/collagen material.

In order to produce the biological parts, when the cells have immigrated into the structural component, they are to be fixed at the site thereof in order to prevent them emigrating into the environment and to ensure a stable architecture of the biological part produced. For this purpose, the active agent complex contains one or more adhesion components by means of which the immigrant cells can be fixed at the site of the structural component. Thus the adhesion component is "anchored", on the one hand, to the cells building up the biological parts and, on the other hand, to the macromolecular network of the structural component. Adhesions of this type are known and display a given degree of anchorage specificity. Examples thereof are albumen bodies of the fibronectin or laminin type, by means of which, for example, connective tissue cells or epithelial cells can be anchored to the structural component. Numerous further adhesion factors of different degrees of specificity are available and are used according to the biological part to be produced in the case of the active agent complex according to the invention. These include, inter alia, the cell adhesion molecules L-CAM, N-CAM, the matrix adhesion molecules cytotactin, tenascin, laminin, fibronectin, collagen type IV, V, VII, and synthetic peptides, which are partial sequences of various adhesions, and transmembrane-connection proteins such as integrin, for example.

In order to increase the specificity of the attachment of the desired cells to the structural component when the biological parts are produced, antibodies against undesired adhesion components can be used. The biological activity of the adhesion components can be measured in different types of adhesion tests (e.g., by means of centrifugal forces, et cetera) and can thus be standardized for the entire active agent complex.

Frequently, the number of cells for producing the biological part which are attracted chemotactically in the vicinity of the structural components and fixed by the suitable adhesin is insufficient for them to constitute the biological part. In addition, the mobile cells available in an organism for these processes in most cases are not in a sufficiently matured state to perform all the functions of a biological part. On the contrary, they are frequently precursors or parent cells from which the operative, mature cells of the biological part to be produced firstly have to develop. For this purpose, the active agent complex according to the invention comprises at least one growth and/or maturation component, preferably in the form of one or more cytokinins, under the effect of which the number of immigrant cells is increased and furthermore the cells mature.

Cytokinins are substances of different chemical structures which are characterized in that they interact with cells and influence their division and growth behavior as well as their maturing and biosynthesis capacity. Thus cytokinins have a hormone-like effect, but in contrast to hormones, do not develop this effect at a distance but rather in localized regions, which is advantageous in the case of the production of biological parts since it is likewise a localized process.

A plurality of different cytokinins of different specificity are known to the person skilled in the art. They can be used for influencing cell growth, differentiation and maturation and for influencing the metabolism of the immigrant cells as a further component in the active agent system according to the invention. The specificity of cytokinins for given cells is determined by the presence of the corresponding receptors on the target cells, the interaction of a cytokinin with the receptor triggering the cellular consequent processes. The receptors mentioned in this case on the target cells are membrane proteins which interact with the chemotactic substance used, bond it and lock into the interior of the cell.

As a result of recycling the receptors, they are always available for bonding the chemotactic substance.

It is similar with the receptors for the respective cytokinins used such that it is only a matter of a different specificity with a similar mechanism of the interaction. While the bonding of the chemotactic substance leads to a directed movement of the target cells, the bonding of the cytokinins to the corresponding receptor of the target cells results in growth and/or differentiation. In many cases the receptors are not yet characterized molecularly such that they are only recognized by their specificity for the relevant legends (chemotactic substances, cytokinin, et cetera).

In this connection the fact should be taken into account that frequently stimulating or inhibiting consequent processes can be triggered at the cells according to the specificity of the cytokinin used and the targeted cells. The cellular consequent process of the cytokinin interaction required for the production of biological parts is in most cases connected to a dual signal relaying process such that advantageously at least two cytokinins are used in the case of the active agent complex according to the invention in order to achieve growth and differentiation. After interaction with a cytokinin many cells produce further cytokinins and release the latter, it then being possible for them thus to stimulate or inhibit themselves (so-called autocrine mechanism).

At times not so rare, the specificity of the cells for given cytokinins also varies with individual differentiation steps such that no further interaction occurs or the reaction of a stimulating cellular consequent process can change into an inhibiting cellular consequent process. The properties of a plurality of cytokinins are known such that the cytokinin effect in the active agent system can likewise be standardized.

Examples of cytokinins are, for example, the colony-stimulating factors in the production of blood, the fibroblast growth factor in the production of connective tissue, the epidermal growth factor in the production of skin, the cartilage-inducing factor in the production of cartilage, the lymphocyte-activating factor as well as spleen peptides in the production of the spleen or the lymph nodes, the T-cell growth factor and thymus peptides for the production of thymus, the bone growth factor and the transforming growth factor for the production of bones, the angiogenesis factor for the production of blood vessels. Furthermore, the following cytokinins are also used: interleukins, insulin-like growth factors, tumor necrosis factor, prostaglandins, leucotrienes, transforming growth factors, growth factors originating from thrombocytes, interferons and growth factors originating from endothelial cells.

Since biological parts in many cases are composed of a plurality of cell types, combinations can occur. Thus, for example, the production of blood vessels is important for the supply of the biological part produced such that an accelerated vessel production is produced/used by adding the angiogenesis factor as the cytokinin component of the active agent system. similarly, the accelerated formation of nerve connections which can be brought about by a corresponding use of additional cytokinins in the active agent complex can be important.

In the following, the invention will be described in further detail with reference to an embodiment.

EXAMPLE 1

Production of a bone-forming active agent complex from cattle bones.

Cattle bones are cleaned, ground and decalcified. The resultant bone matrix is the initial complex for the application of the process according to the invention. The bone matrix is mixed with a solution of a suitable denaturing agent, for example, urea, and agitated at 10° C. for 24 hours. In principle redox reactions, enzyme-catalyzed conversions, reactions with chaotropic salts, variations of pH, temperature or ionic strength, mechanical effects, substances with surfactant properties (detergents) are used as denaturing means.

The portions of the bone matrix which are homogeneous in solution are separated off. This can be performed by filtration or centrifugation, for example. The portion in the homogenous phase is divided at a volume ratio of 1:1. One part of the denatured homogenous phase divided in this way is fractionated, which can be achieved by chromatography, electrophoresis, ultrafiltration or dialysis. In accordance with the invention, the resultant desired fraction is now added to the second part of the denatured, homogenous phase and renatured together with the latter.

Renaturing occurs by removing the denaturing agent, for example, by filtration. In general, various physical, chemical or biological processes can be used here. The resultant final complex is the active agent complex suitable for forming bones.

EXAMPLE 2

10 kg of a biological material (e.g., connective tissue) are mixed with 80 liters of an aqueous solution of a low-molecular weight denaturing agent (e.g., 6 molar urea) and agitated at room temperature for 72 hours.

The dissolved portions are separated from the insoluble residue by a suitable separating process, for example, by centrifuging the solution. The denatured supernatant is divided, for example, at a volume ratio of 1:1. From part 1 the low-molecular active agent fractions up to a desired molar mass, for example, 30000 Daltons, are enriched and the high-molecular substrate portion removed, for example, for means of filtration, on a suitable ultrafilter in a hollow fiber filter cartridge.

The active agent fraction enriched and separated in this manner is now not, as in the prior art, processed with respect to the active agent but combined with part 2 of the denatured supernatant and delivered for renaturing in the presence of the high-molecular substrate. Renaturing is performed by removal of the denaturing agent, for example, urea. In this respect, the active agent complex is formed as a result of the substrate combining with the active agents and the renaturing of the substrate encouraging the renaturing of the active agents. By repeating the denaturing-renaturing cycle, the substrate can be saturated with active agents until the active agent complex optimized for the desired biological effects is produced. Lyophilization can be used for isolating the active agent complex.

Thus made-to-measure active agent complexes can be produced for very different applications as a result of structural, chemotactic substances, adhesive, proliferative, differentiating properties being obtained in the active agent complex according to the invention in accordance with this process.

Other properties can relate, for example, to the immunogenity, toxicity, et cetera, and can be deliberately controlled in the active agent complex by means of the production process according to the invention.

Further areas of application for active agent complexes produced according to the process of the invention lie within the field of the modification of interfaces for increasing biocompatibility or for achieving given reactions with cells. For example, in the cultivation of cells for biotechnological or research purposes, technical coatings with active agent complexes of this type are important. Applications are also used extracorporeal in the case of diagnostic or therapeutic systems, such as dialyzers and oxygenators, for example, or, in the case of artificial organs, intracorporally.

Although only preferred embodiments are specifically illustrated and described herein, it will be appreciated that many modifications and variations of the present invention are possible in light of the above teachings and within the purview of the appended claims without departing from the spirit and intended scope of the invention.

I claim:

1. A method for producing bone active ingredient complexes comprising the steps:

dissolving demineralized bone in a protein denaturing process, denaturing said proteins in demineralized bone, thus obtaining a homogeneous phase containing denatured proteins;

separating said homogeneous phase from the undissolved residue;

dividing the homogeneous phase into at least two parts and fractionating at least one of said parts with respect to at least one of the following desired components:

a support component comprising a macromolecular gel of collagen and/or proteoglycans;

an adhesion component capable of selectively binding bone precursor cells to the support component;

a chemotactic component capable of attracting bone precursor cells to the support component;

a growth and maturation component capable of stimulating bone precursor cells to mature into bone cells;

combining at least one of the obtained desired fractions with the other parts of the homogeneous phase to form a final complex; and renaturing the final complex to form the active ingredient complex.

2. A method for producing cartilage active ingredient complexes comprising the steps:

dissolving cartilage in a low molecular weight denaturing agent, denaturing cartilage proteins contained therein, thus obtaining a homogeneous phase containing denatured cartilage proteins;

separating the homogeneous phase from the undissolved residue;

dividing the homogeneous phase into at least two parts;

fractionating at least one of these parts into a low molecular weight fraction and a high molecular weight fraction;

removing the high molecular weight fraction and further fractionating the low molecular weight fraction for at least one of the following components:

an adhesion component capable of selectively binding cartilage precursor cells to the support component;

a chemotactic component capable of attracting cartilage precursor cells to the support component;

a growth and maturation component capable of stimulating cartilage precursor cells to mature into cartilage cells;

combining at least one of the obtained desired fractions with the other parts of the homogeneous phase to form a final complex; and renaturing the final complex to form the active ingredient complex.

3. The method of claim 1, wherein the homogenous phase is divided into two parts, the first part is fractionated and the fractions assayed for the support component, adhesion component, chemotactic component and growth and maturation component, and the fractions containing at least one of the desired components are then added to the second part to form the final complex.

4. The method of claim 1, wherein at least one growth and maturation component is a cytokine.

5. The method of claim 1, wherein the cytokine is either a bone-derived or non-bone extracted cytokine.

6. The method of claim 1, wherein protease inhibitors are added to the active ingredient complex.

7. The method of claim 1, wherein at least one immunosuppressant or anti-inflammatory compound is added to the active ingredient complex.

8. The method of claim 7, wherein the immunosuppressants or anti-inflammatory compounds are selected from phospholipase inhibitors, cyclooxygenase inhibitors, lipoxygenase inhibitors and cyclosporins.

9. The method of claim 1, wherein the chemotactic component is selected from chemotactic peptides, arachidonic acid derivatives and mixtures thereof.

10. The method of claim 1, wherein the adhesive component is selected from fibronectin, tenascin, cycotactin, laminin, chondronectin, collagen types IV, V, VII, IV, N-CAM, L-CAM or integrin proteins or mixtures thereof.

11. The method of claim 1, wherein the growth and maturation component is selected from the group consisting of colony-stimulating factor (CSF), interleukin (IL), insulin-like growth factor (IGF), prostaglandins (PG), leukotrienes (LT), transforming growth factor (TGF), fibroblast growth factor (FGF), interferons (IFN), epidermal growth factor (EGF), bone derived growth factor (BDGF), growth factor originating from thrombocytes (PDGF) and mixtures thereof.

12. The method of claim 1, wherein the growth and maturation component includes at least one angiogenesis factor, nerve growth factor and mixtures thereof.

13. The method of claim 1, wherein each of said support, adhesion, chemotactic and maturation components is different.

14. The method of claim 1 wherein the active ingredient complex is lyophilized.

15. The method of claim 3 wherein the active ingredient complex is lyophilized.

16. The method of claim 2, wherein the homogeneous phase is divided into two parts, the first part is fractionated as in claim 2, and the desired fractions are added to the second part, to form the active ingredient complex.

17. The method of claim 2, wherein at least one of the growth and maturation components is a cytokine.

18. The method of claim 17, wherein the cytokine is either a cartilage derived or non-cartilage extracted cytokine.

19. The method of claim 2, wherein protease inhibitors are added to the active ingredient complex.

20. The method of claim 2, wherein at least one immunosuppressant or anti-inflammatory substance is added to the active ingredient complex.

21. The method of claim 20, wherein the immunosuppressants or anti-inflammatory compounds are selected from phospholipase inhibitors, cyclooxygenase inhibitors, lipoxygenase inhibitors and cyclosporins.

22. The method of claim 2, wherein the chemotactic component is selected from chemotactic peptides, arachidonic acid derivatives and mixtures thereof.

23. The method of claim 2, wherein the adhesive component selected from fibronectin, tenascin, cycotactin, laminin, chondronectin, collagen type IV, V, VII, N-CAM, L-CAM or integrin proteins or mixtures thereof.

24. The method of claim 2, wherein the growth and maturation component is selected from the group consisting of colony stimulating factors (CSF), interleukins (IL), insulin-like growth factors (IGF), prostaglandins (PG), leukotrienes (LT), transforming growth factors (TGF), fibroblast growth factors (FGF), interferons (IFN), epidermal growth factors (EGF), bone derived growth factors (BDGF), growth factor originating from thrombocytes (PDGF) and mixtures thereof.

25. The method of claim 2, wherein the maturation component is selected from the group consisting of angiogenesis factors, nerve growth factors and mixtures thereof.

26. The method of claim 2, wherein each of said support, adhesion, chemotactic and maturation components is different.

27. The method of claim 2 wherein the active ingredient complex is lyophilized.

28. The method of claim 16 wherein the active ingredient complex is lyophilized.

* * * * *